United States Patent
Sandham et al.

(10) Patent No.: US 11,844,504 B2
(45) Date of Patent: Dec. 19, 2023

(54) RADIOLUCENT SURGICAL RETRACTOR

(71) Applicant: Axis Spine Technologies Ltd., St. Albans (GB)

(72) Inventors: Nick Sandham, London (GB); Eddie Hamilton, London (GB); Jonathan Lloyd Arcos, St. Albans (GB); Christopher Reah, Somerset (GB); John Sutcliffe, Essex (GB); Patrick Joseph McKenna, Berkshire (GB); Obi Agu, London (GB)

(73) Assignee: Axis Spine Technologies Ltd., St. Albans (GB)

( * ) Notice: Subject to any disclaimer, the term of this patent is extended or adjusted under 35 U.S.C. 154(b) by 0 days.

(21) Appl. No.: 17/024,820

(22) Filed: Sep. 18, 2020

(65) Prior Publication Data
US 2021/0085307 A1    Mar. 25, 2021

Related U.S. Application Data

(60) Provisional application No. 62/903,255, filed on Sep. 20, 2019.

(51) Int. Cl.
*A61B 17/02* (2006.01)
*A61B 17/00* (2006.01)

(52) U.S. Cl.
CPC ........ *A61B 17/0206* (2013.01); *A61B 17/025* (2013.01); *A61B 17/0293* (2013.01);
(Continued)

(58) Field of Classification Search
CPC .... A61B 2017/0212; A61B 2017/0256; A61B 1/32; A61B 17/02; A61B 17/0206; A61B 17/025; A61B 17/0293
See application file for complete search history.

(56) References Cited

U.S. PATENT DOCUMENTS 6,139,493 A * 10/2000 Koros ............... A61B 17/0206
                                                          600/231
6,206,826 B1 * 3/2001 Mathews ............ A61B 17/025
                                                          600/210
(Continued)

FOREIGN PATENT DOCUMENTS

CN        108670327 A      10/2018
WO      2013074396 A1      5/2013
(Continued)

OTHER PUBLICATIONS

International Search Report corresponding to international application No. PCT/IB2020/000751, dated Jan. 12, 2021. (14 pages).
(Continued)

*Primary Examiner* — Eduardo C Robert
*Assistant Examiner* — Steven J Cotroneo
(74) *Attorney, Agent, or Firm* — Maginot, Moore & Beck LLP

(57) ABSTRACT

A self-supporting surgical retractor is provided for retracting soft tissue and anatomy at a spinal surgical site. The retractor includes a tubular base defining an upper rim and a lower rim and a working channel there between the upper and lower rims, in which the base and lower rim are sized and configured to be seated on adjacent vertebral bodies spanning an intervertebral space. At least two elongated legs are provided, each projecting from the upper rim and each including a fixation feature at a free end thereof. Each of the legs has a length sufficient for the fixation feature to be outside the body of a patient when the lower rim is seated on adjacent vertebral bodies of the patient. The retractor is formed of a radio-transparent or radio-lucent material.

26 Claims, 31 Drawing Sheets

(52) U.S. Cl.
CPC ............... *A61B 2017/0092* (2013.01); *A61B 2017/0256* (2013.01)

(56) References Cited

U.S. PATENT DOCUMENTS

| | | | | |
|---|---|---|---|---|
| 6,464,634 | B1* | 10/2002 | Fraser | A61B 17/0293 600/233 |
| 6,517,544 | B1* | 2/2003 | Michelson | A61B 17/1659 606/85 |
| 8,795,167 | B2* | 8/2014 | Ainsworth | A61B 1/32 600/222 |
| 9,867,605 | B2* | 1/2018 | Adams | A61B 17/0206 |
| 2001/0037054 | A1* | 11/2001 | Weinstein | A61B 17/0206 600/210 |
| 2002/0116006 | A1* | 8/2002 | Cohen | A61F 2/446 606/99 |
| 2003/0004401 | A1* | 1/2003 | Ball | A61B 17/06061 600/233 |
| 2003/0135217 | A1* | 7/2003 | Buttermann | A61B 17/1757 606/79 |
| 2005/0043740 | A1* | 2/2005 | Haid, Jr. | A61B 17/1757 606/90 |
| 2006/0200186 | A1* | 9/2006 | Marchek | A61B 17/0218 606/191 |
| 2007/0260125 | A1* | 11/2007 | Strauss | A61B 17/0218 600/219 |
| 2007/0276191 | A1 | 11/2007 | Selover et al. | |
| 2008/0132766 | A1* | 6/2008 | Dant | A61B 17/02 600/219 |
| 2008/0300465 | A1* | 12/2008 | Feigenwinter | A61B 17/0293 606/90 |
| 2009/0203969 | A1* | 8/2009 | Cohen | A61B 17/0206 600/245 |
| 2009/0216234 | A1 | 8/2009 | Farr et al. | |
| 2010/0228095 | A1* | 9/2010 | Warren | A61B 1/32 600/210 |
| 2011/0112586 | A1* | 5/2011 | Guyer | A61B 17/0293 606/86 R |
| 2011/0196208 | A1* | 8/2011 | Warren | A61B 17/0293 600/210 |
| 2013/0006061 | A1* | 1/2013 | Alexander | A61B 1/32 600/235 |
| 2013/0150681 | A1* | 6/2013 | O'Prey | A61B 17/0293 600/206 |
| 2015/0080973 | A1* | 3/2015 | Eastlack | A61F 2/4611 606/86 A |
| 2015/0366548 | A1* | 12/2015 | Lauchner | A61B 90/30 600/206 |
| 2017/0333021 | A1* | 11/2017 | Heiges | A61B 17/0218 |
| 2017/0333023 | A1* | 11/2017 | Adams | A61B 17/0218 |
| 2020/0245856 | A1* | 8/2020 | Berry | A61B 1/32 |

FOREIGN PATENT DOCUMENTS

| | | |
|---|---|---|
| WO | 2017200555 A1 | 11/2017 |
| WO | 2018156638 A1 | 8/2018 |
| WO | 2018165365 A2 | 9/2018 |

OTHER PUBLICATIONS

International Search Report corresponding to International application No. PCT/IB2020/000751 dated Apr. 1, 2021 (22 pages).

* cited by examiner

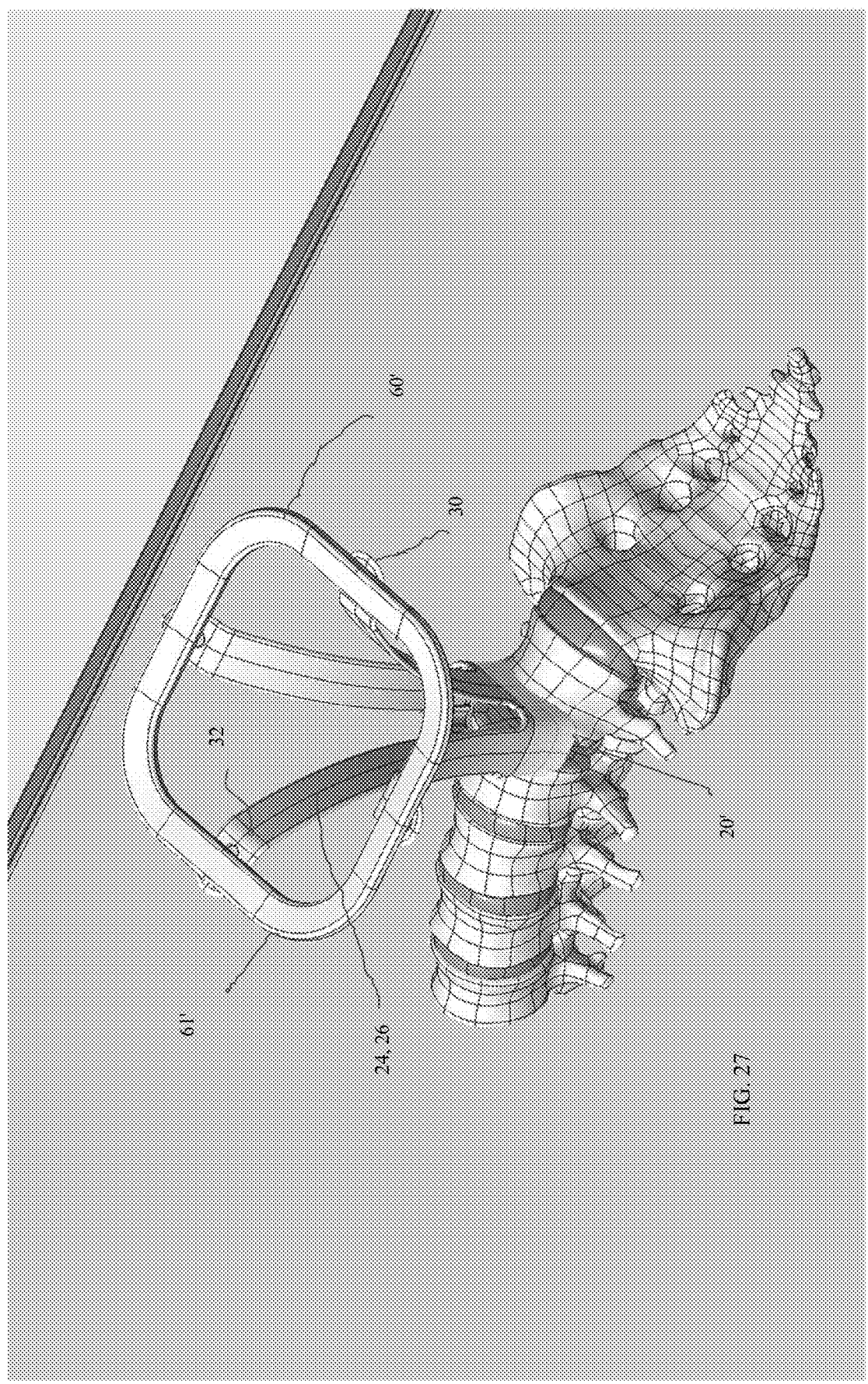

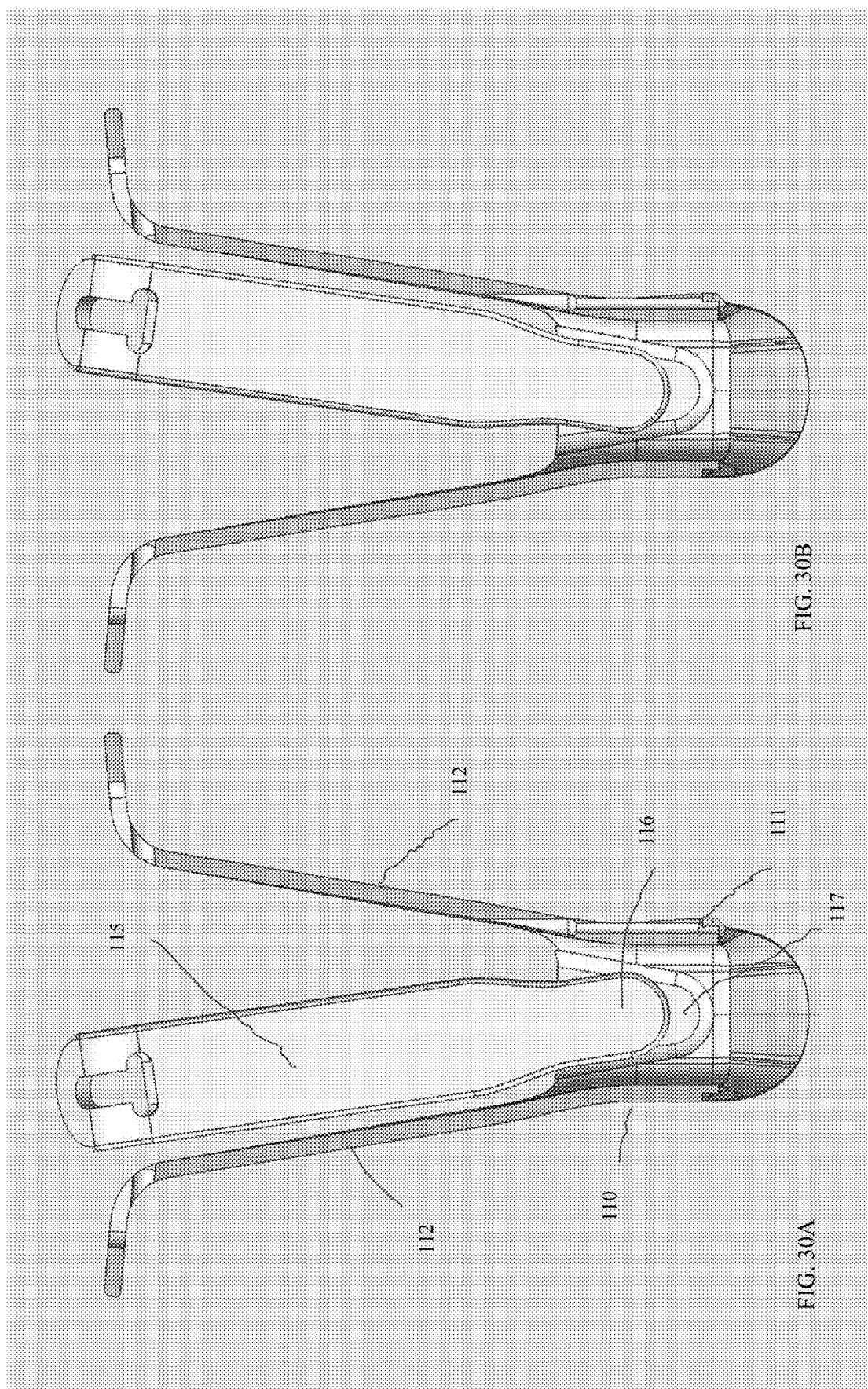

RADIOLUCENT SURGICAL RETRACTOR

REFERENCE TO RELATED APPLICATION AND PRIORITY CLAIM

This application is a utility filing from and claims priority to U.S. Provisional Application No. 62/903,255, filed on Sep. 20, 2019, the entire disclosure of which is expressly incorporated herein by reference.

BACKGROUND

The present disclosure relates to tissue retractors for use in surgical procedures to retract tissue and/or organs at a surgical site.

In general terms, a retractor is a surgical instrument used to separate the edges of a surgical incision or wound, as shown in FIG. 1. Retractors can also be configured to hold back underlying organs and tissue so that other parts of the body may be accessed by the surgeon. A wide variety of surgical retractors are available, depending on the requirements for the particular surgical procedure and, in some cases, surgeon preference. The simplest retractor is a hand-held device, such as the retractor shown in FIG. 2. The hand-held device includes a handle, an elongated body and a curved blade configured to engage the edges of the wound. This type of retractor is held by a surgeon or medical assistant throughout the surgical procedure, which can be a detriment due to the potential for fatigue. However, the hand-held retractor provides a degree of flexibility not easily accomplished by other retractors in that the tissue/organs being retracted can be directed by the operating surgeon.

A variant from the hand-held retractor is the self-retaining retractor, such as the retractors shown in FIG. 3. The self-retaining retractors are typically in a scissors or sliding mount form. In these types of devices blades are provided at the ends of at least two arms, with the arms coupled to each other (scissors-type) or mounted on a separate beam (sliding mount). The self-retaining retractors are held in position at the surgical site by the tension applied to the edges of the incision and typically rest on the patient's body.

A common type of retractor is the frame-type retractor, as depicted in FIG. 4. In this type of device, a rigid frame is formed to define the eventual perimeter of the surgical incision. The rigid frame is anchored to the operating table to hold the frame in the desired position. Individual retraction arms are mounted to the frame and manipulated to engage and retract the edges of the incision. A variation of the frame-type retractor is the cable-winch retractor in which the rigid frame is offset from the patient, acting as a rigid support for a cable-winch system used to pull retractor blades toward the frame. This type of frame retractor has the advantage of keeping the surgical site relatively free of equipment that can hamper access by the surgeon.

Tubular retractors are another common surgical device. As depicted in FIG. 5, the tubular retractor is essentially a tube that is manipulated into the surgical site, sometimes with the assistance of peripheral retractors. The tubular retractor creates a working channel through which various devices, instruments and implants are introduced. The tubular retractors can be self-retaining or anchored to a separate rigid frame. A split-blade retractor, as shown in FIG. 6, is a variation of the tubular retractor in that the walls of the tube are outwardly movable to increase the volume of the working space defined by the retractor. The split-blade retractor starts out as a closed tube for introduction into the incision, and then expanded as needed.

The typical surgical retractor is formed of a metal, such as stainless steel, in order to provide sufficient strength and rigidity, as well as sterilizability. One drawback of the conventional metallic retractor is that the metal is generally radio-opaque. In some open surgical procedures, such as spinal surgeries, it can be necessary to obtain an X-ray image in order to verify the local anatomy and/or the orientation of instruments and implants. The radio-opaque retractor component can thus obscure or even hide parts of the surgical field that may be important to the surgeon. Some retractors are made of a less radio-dense metal, such as aluminum, to retain the benefits of stainless steel with less impact on the ability to image the surgical site.

The operating room is equipped with overhead lights that can be positioned and oriented to illuminate the surgical field. However, it is difficult to position the limited number of lights (usually two per OR) to avoid shadows from the surgeon(s) and attending medical personnel. One option has been to provide the surgeon with a headlight system which avoids the problem with shadows. However, it is still often difficult for the surgeon to direct the light beam(s) where it is needed while also performing the surgical procedure. To address the problems with these approaches, some retractor systems include lighting components associated with the retractor structure, such as the system shown in FIG. 7. Fixed retractor systems can include one or more lights mounted to the same fixed frame on which the retractors are mounted. In another approach, the retractor blade itself is provided with a lighting component integrated into the blade to directly illuminate the space adjacent the retractor. One detriment is that the addition of lighting to the retractor system takes up space in the surgical site and adds complexity to the retractor set up.

One typical spinal surgical procedure relies on an anterior approach in which the spine is accessed through the abdomen of the patient, as shown in FIG. 8. The size of the wound required for an anterior approach can vary, but is usually limited to a working channel diameter of 7-10 cm. Frame retractors are typically used to retract the edges of the incision, as well as to hold critical blood vessels. In particular, the aorta and vena cava must be moved and held in place to provide clear access to the lower lumbar and sacral vertebrae. Due to the nature of the surgery, the retractors may get contacted or the spine may move as it is being manipulated, which in turn may cause the blood vessels to become dislodged from the retractor and creep into the surgical field.

Anterior spinal surgery also involves other specialized instrumentation, such as retractor shims, as shown in FIG. 9, and paddles, as shown in FIG. 10. Retractor shims are locked to the existing retractor blades and used to either anchor the retractor blade or increases the effective area of the blade. In the former case, the shim can include a spike or screw that can be driven into a vertebral body to hold the retractor in position during the surgery. In the latter case, the shim can be used to lengthen or widen the retractor blade to increase the amount of tissue being held back by the retractor. Shims are commonly used on split blade retractors.

The paddle (FIG. 10) is an instrument that is introduced into the space between vertebral bodies after the intervertebral disc has been removed. The paddle can be a distractor that is used to separate the adjacent vertebral bodies, or a sizer that is used to determine the size of an implant to be introduced into the space. Although the paddle instrument is not part of the distractor system, it is a crucial instrument used in anterior spinal surgeries that must be accommodated by the retractor system.

In view of the benefits and detriments of prior retractor systems, there remains a need for a retractor that is radio-transparent or radio-lucent yet still sturdy enough to keep the surgical space open throughout the surgery. There is also a need for a single use, disposable retractor system that eliminates the need for sterilization for re-use and reduces the overall cost of the retractor instrumentation.

SUMMARY OF THE DISCLOSURE

The present disclosure provides a retractor system particularly suited for use during anterior spinal surgeries. In one feature the primary components of the retractor system are formed of a radio-transparent or radio-lucent material, such as a plastic material. At the core of the retractor system is a retractor component that has a structure similar to a tubular retractor, with additional features that help hold the retractor to the spine during the procedure and prevent the adjacent blood vessels from creeping back into the surgical field. The system includes connector components for lengthening or shortening the retractor, and shims that can be used as a disc space distractor.

DESCRIPTION OF THE FIGURES

FIG. 27 is a perspective view of a self-supporting retractor system according to another embodiment of the present disclosure.

FIGS. 30A, B are side views of a retractor system according to a further embodiment incorporating movable legs.

DETAILED DESCRIPTION

Figure 1:
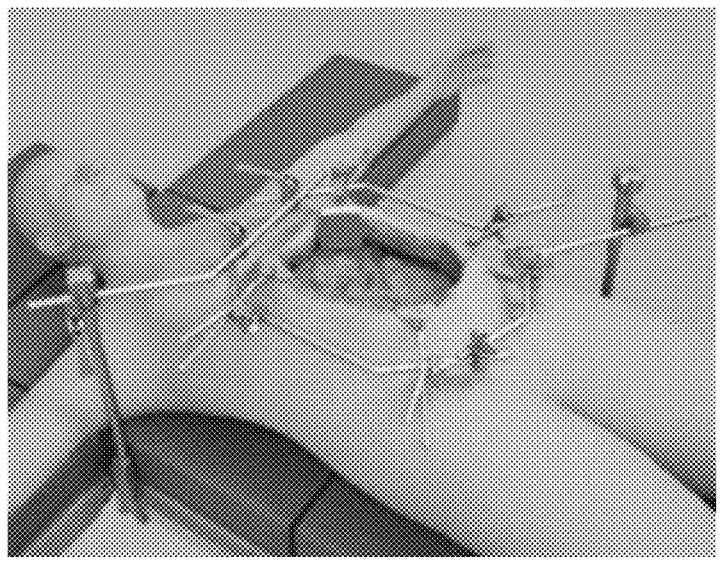
FIG. 1 is pictorial view of one type of surgical retractor of the prior art shown in use.
Figure 2:
FIG. 2 is a pictorial view of a hand-held surgical retractor of the prior art.
Figure 3:
FIG. 3 are pictorial views of self-retaining surgical retractors of the prior art.
Figure 4:
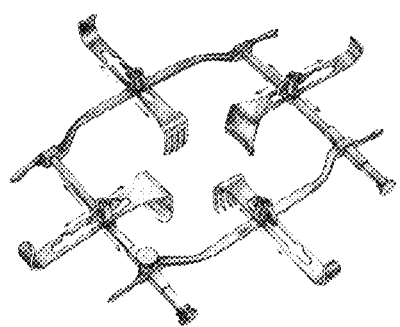
FIG. 4 is a pictorial view of a frame-type retractor system of the prior art.
Figure 5:
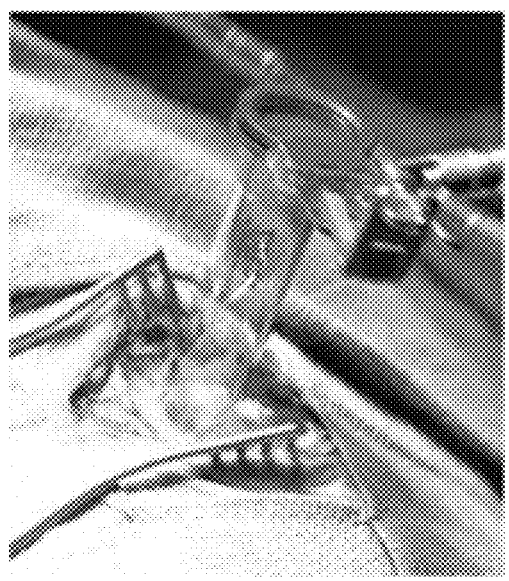
FIG. 5 is a pictorial view of a tubular retractor of the prior art.
Figure 6:
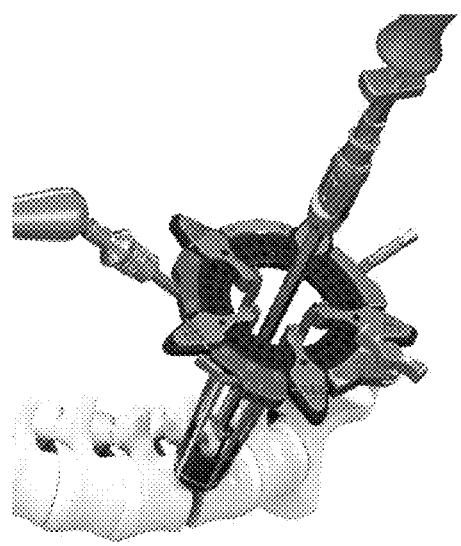
FIG. 6 is a pictorial view of a split blade retractor of the prior art.
Figure 7:
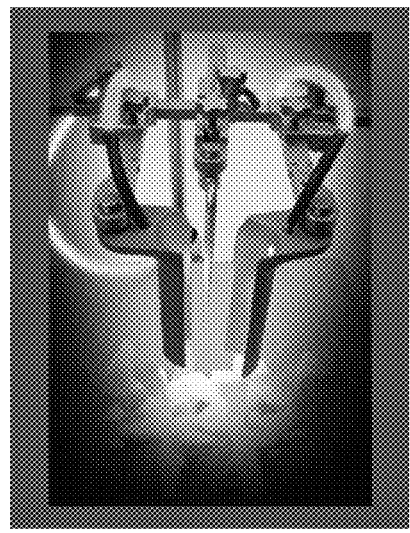
FIG. 7 is a pictorial view of a retractor-based lighting system of the prior art.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 8:
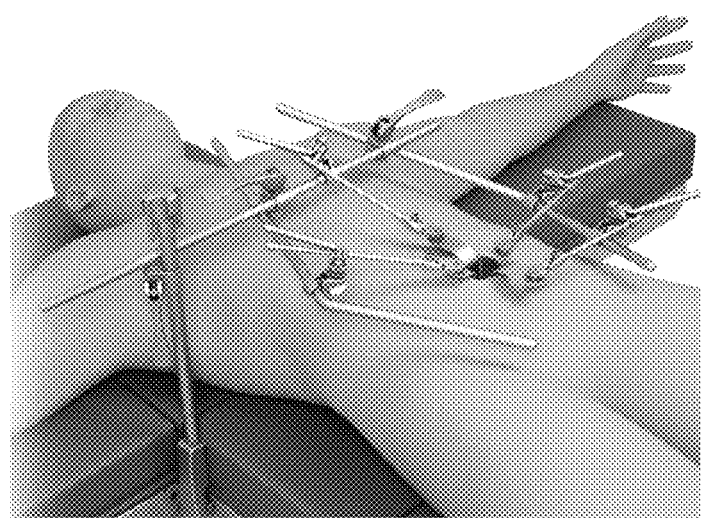
FIG. 8 is a pictorial representation of an anterior retractor system of the prior art for use in anterior spinal surgery.
Figure 9:
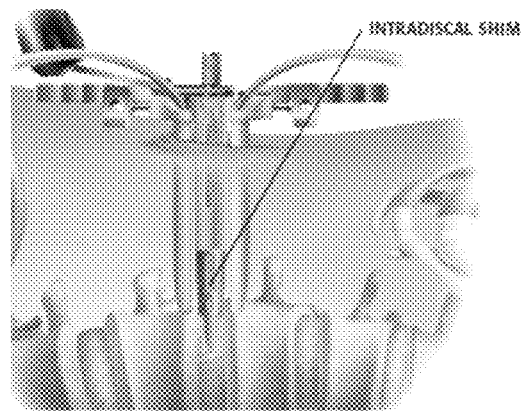
FIG. 9 is a diagram of a shim of the prior art used with surgical retractors.
Figure 10:
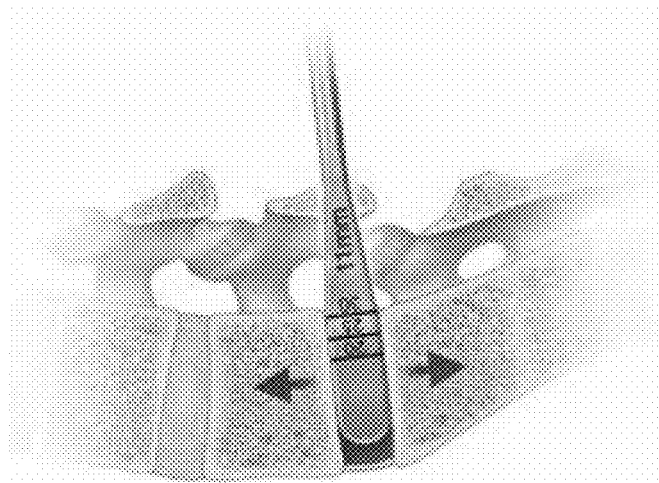
FIG. 10 is a diagram of a distractor of the prior art used in spinal surgery.
Figure 11A:
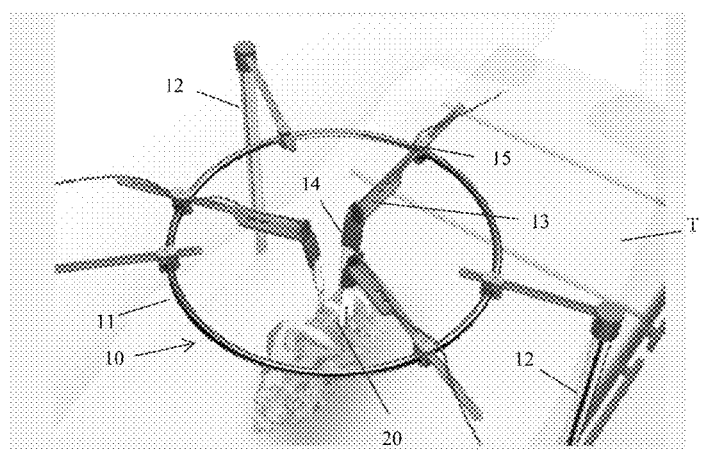
FIGS. 11A-C are pictorial views of a surgical retractor system according to one embodiment of the present disclosure, showing the system relative to the patient's anatomy during an anterior spinal surgery.
Figure 11B:
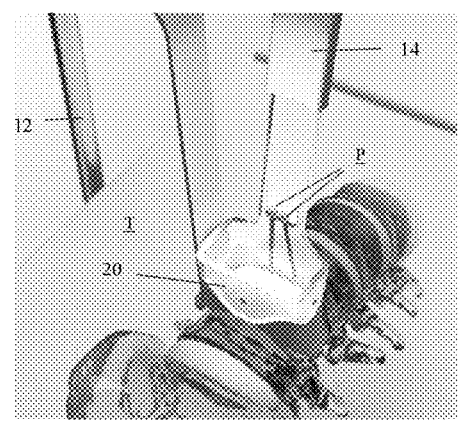
Figure 11C:
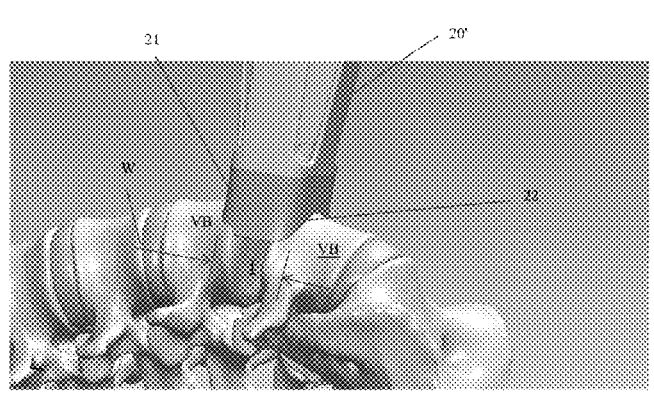

A retractor system 10 according to the present disclosure is shown in FIGS. 11A-11C, in which the system is a frame-based system. The system 10 is shown in use in an anterior lumbar surgical procedure. However, it is understood that the retractor system disclosed herein can be used in other surgical procedures, such as, but not limited to, cervical spine procedures and posterior facet surgery. The system 10 includes a frame 11 that is fixed to the operating table T by mounting components 12. The mounting components 12 can be known mounting components for use in supporting surgical retractors or frames for retractors, such as the mounting components depicted in FIGS. 1 and 8. The frame 11 can be a circular ring that is sized to avoid interference with the surgical site. The core of the present retractor system is the retractor 20 that retracts the tissue, blood vessels and organs, and defines a working channel for anterior access to the spine. The retractor 20 is supported on the frame 11 by brackets 13 with an engagement portion 14 that engage a leg of the retractor, as described in more detail herein. The brackets 13 are adjustably fastened to the frame 11 by clamping elements 15.

Figure 12A:
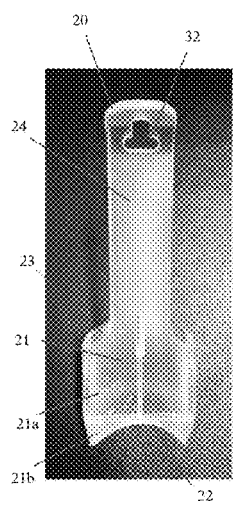
FIGS. 12A-B are end and side views of a retractor for use in the retractor system shown in FIGS. 11A-C.
Figure 12B:
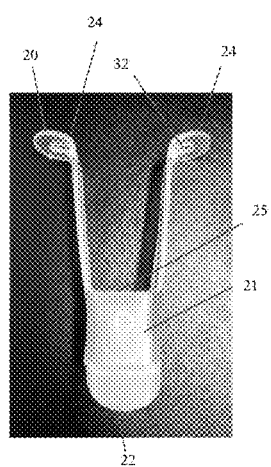

In one embodiment shown in FIGS. 12A-12B, the retractor 20 includes a generally rectangular saddle-shaped tubular base 21 that defines a working channel 23 that is sized to receive surgical instruments and implants. The base 21 includes a lower rim 22 that is configured to generally conform to the vertebral bodies on either side of the intervertebral space, as shown in FIG. 11C. In particular, the lower rim 22 can have a curvature that follows the curvature of the vertebral bodies VB at the point of surgical approach (i.e., anterior or posterior). It can be appreciated that the tubular base is sized to span the intervertebral space I so that the lower rim 22 can have adequate purchase on the adjacent vertebral bodies VB. Thus, the base 21 has a width W (FIG. 11C) that is greater than the width of the intervertebral space I. As shown in FIG. 12A, the lower rim 22 has a concave curvature that corresponds to the curvature of the vertebral bodies. The length L of the curved rim 22 is sufficient for the base 21 to form a solid foundation for the retractor when seated on the vertebral bodies VB. It can be appreciated that the curvature of the lower rim and the dimensions W, L of the generally rectangular base 21 are determined by the dimensions of the intervertebral space and vertebral bodies at the particular spinal level.

Retractor 20 further includes a pair of projecting legs 24 projecting upward from the upper rim 25. In one embodiment, the legs are integral with the base 21. The legs define a fixation feature 32 that is engaged by the engagement portion 14 of the brackets 13 (FIG. 11A), so that the retractor can be held in position by the fixed frame. Thus, the legs have a length from the upper rim that is sufficient for the fixation features to be outside the patient, and more particularly at a height of 7-10 cm above the patient's body. In a specific embodiment, the legs 24 have a length of 15-20 cm, while the base 21 has a height of 4-6 cm from the lower rim to upper rim.

In one feature of the disclosure, the retractor 20 is integrally formed so that the legs 24 are one piece with the base 21. The retractor 20 is formed of a radio-transparent or radio-lucent material that is sufficiently rigid to hold back the tissue, blood vessels and organs to maintain an adequate working channel for the surgeon. The material can be a thermoplastic, such as nylon, polycarbonates and polyketones, and may be a reinforced composite, such as a carbon-fiber thermoplastic. In another feature, the base 21 includes two portions 21a, 21b, with the upper portion 21a being substantially rigid and the lower portion 21b being generally compliant or flexible. The lower portion 21b defines the lower rim 22 that contacts the vertebral bodies. The flexibility of the lower portion 21b allows the portion to be compressed as the retractor 20 is pushed against the vertebral bodies (or pulled downward when used in a fixed system). The compliance of the lower portion allows it to conform to the local anatomy providing a firm base for seating the retractor.

In one embodiment the two portions 21a, 21b can be formed of the same material using a manufacturing process that allows variation of the durometer or Shore hardness between the two portions. In another approach the compliant portion 21b can be adhered to the rigid portion 21a, or can be molded onto the rigid portion in a two-stage molding process. In an alternative approach, the portions of the base can be produced in an additive or 3D printing process. The hardness and/or flexibility of the base 21 and the portions 21a, 21b can be controlled by the printing process to produce a base having various hardness or flexibility profiles. In one version, the two portions can have distinct hardness/flexibilities, whereas in another version the material properties can be varied at locations throughout the retractor body, meaning that more than two portions have different relative flexibilities/hardnesses. Additive or 3D printing also adds the ability to vary the hardness/flexibility in any direction of the retractor. For instance, the base 21 can have vertical sections of greater or lesser rigidity/flexibility or several horizontal regions of different rigidity/flexibility, all calibrated to retract particular tissue, such as nerves and blood vessels.

Figure 13C:
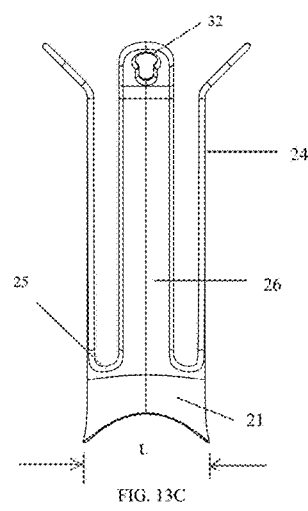
FIGS. 13A-D are perspective, bottom, side and end views of a retractor, according to another embodiment of the disclosure, for use in the retractor system shown in FIGS. 11A-C.
Figure 13D:
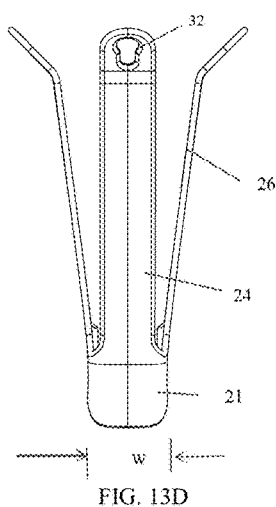
Figure 13B:
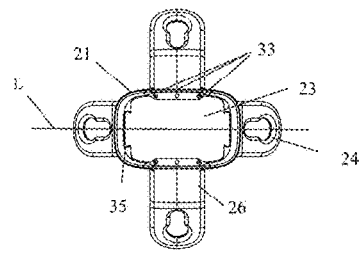
Figure 13A:
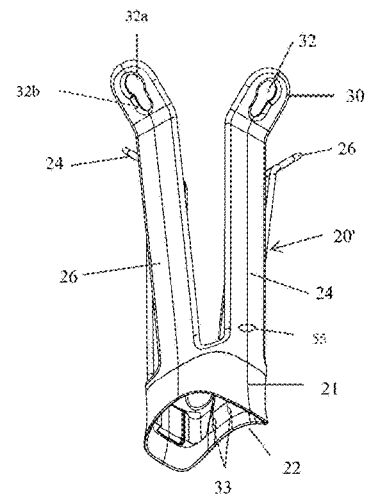
Figure 14:
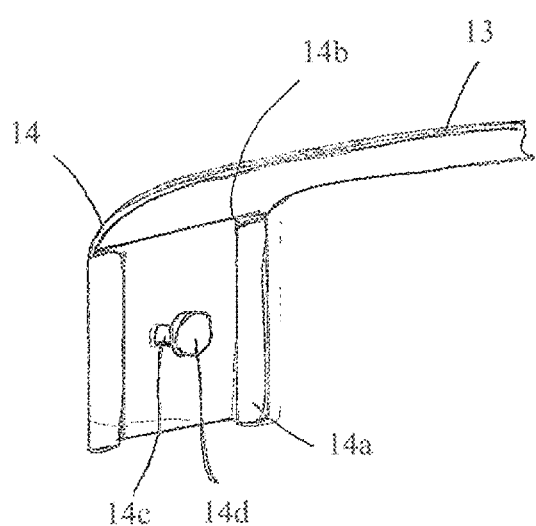
FIG. 14 is a perspective view of an engagement portion of the brackets shown in FIG. 11A.

Another embodiment of a retractor 20' is shown in FIGS. 13A-D. In this embodiment, a pair of upwardly projecting legs 24 is provided at opposite ends of the body 21, and a second pair of legs 26 is provided at opposite sides of the body. As reflected in the view of FIG. 13B, the body is elongated or generally rectangular so that the body can be positioned with its long axis L transverse to the axis of the spine. The body defines a working channel 23 that provides access to the surgical site. The width of the body between the legs 26 is greater than the width of a distracted intervertebral space so that the lower rim 22 can engage the adjacent vertebral bodies (FIG. 11C). The legs 24, 26 each include an angled tab 30 that defines the fixation features 32 that are connected to the engagement portion 14 of the brackets 13 used to connect the retractor to the frame, as described above. The fixation features 32 and engagement portions 14 are configured for removable engagement to allow the retractor to be positioned first within the surgical space and then connected to the frame 11. In one embodiment, the fixation features 32 can be in the form of a keyhole or T-slot to receive a complementary configured connecting pin within the engagement portions 14 of the brackets 13. In one embodiment, the fixation portion can be a slot defined by a large opening 32a and a narrower opening 32b. Thus, as shown in FIG. 14, the engagement portion 14 can include edge panels 14a that define a slot 14b to receive a leg 24, 26. A post 14c includes an enlarged head 14d that can be inserted through the large opening 32a and slid down into the narrower opening 32b to fix the bracket 13 to the leg of the retractor 20'. It can be appreciated that the orientation of the large opening relative to the narrower opening can be reversed from that shown in FIG. 13A depending on the orientation of the bracket 13 engaged to the fixation feature 32. If the bracket is oriented so that it exerts a downward force on the angled tab 30, then the openings 32a, 32b can be arranged as shown in FIG. 13A. On the other hand, if the bracket exerts a slightly upward force, the narrower opening 32b should be above the large opening 32a to retain the post 14c within the fixation feature 32.

Returning to FIGS. 13A-13D, the legs 24, 26 have a length from the base 21 that places the fixation features 32 outside the patient's body and in alignment with the frame 11 for the fixed retractor system 10 (FIG. 11A). The legs 26 can be angled outwardly or laterally from the sides of the base, as shown in FIG. 13D, to help enlarge the working channel and improve access to the intervertebral space beneath the retractor 20'. The legs 24 at the long ends of the retractor are generally vertically oriented, as shown in FIG. 13C, to accommodate shims, as described herein. However, the legs 24 can also flare outwardly in the same manner as legs 26 in alternative embodiments.

In one feature, the body 21 can define a plurality of bores 33 (FIGS. 13A, 13B) extending through the side walls of the body 21 and opening adjacent the rim 22. The bores can receive anchor pins P or screws that can be driven into the adjacent vertebral bodies to solidly anchor the retractor (FIG. 11B), particularly when the retractor is used as part of a self-supporting system.

It is understood that the retractor 20' can be formed of the same material as the retractor 20 discussed above. Moreover, the base 21 of the retractor 20' can be configured like the base shown in FIGS. 12A-12B to include the rigid upper portion 21a and the compliant lower portion 21b.

Figures 15A, 15B, 15C:
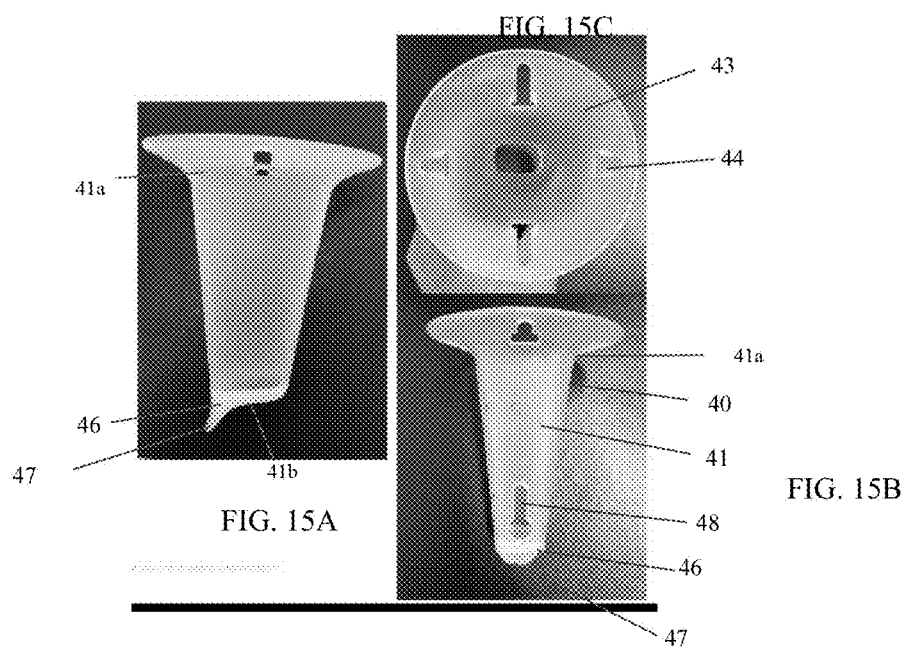
FIGS. 15A-C are views of a retractor for use in the retractor system shown in FIGS. 20A-C.

Another retractor 40 is shown in FIGS. 15A-C that is akin to a conventional tubular retractor. In particular, the retractor 40 includes a frusto-conical tubular base 41 having a generally elliptical or elongated cross-section similar to the retractor 20' described above. Unlike the prior retractors 20, 20', the body 41 of the retractor 40 spans the space between the vertebral bodies and the fixation frame 11 (FIG. 11A). The upper rim 41a of the body merges into a shallow disc 43 which defines the fixation features 44 for engaging the fixation frame to the retractor 40. The disc 43, and particularly the fixation features 44, define a diameter that is substantially the same as the diameter of the fixation frame 11 so that the frame can be engaged directly to the disc without the need for the brackets 13. The lower portion 46 of the base 41 is open and defines the lower rim 41b for passage or tools, instruments and implants into the surgical site. As with the other self-supporting retractors, the lower rim 41b is configured to engage the surface of adjacent vertebral bodies. The lower portion 46 can thus be compliant or flexible, like the lower portion 21b of the retractor 20 described above. The lower portion 46 need not be symmetrical but may instead adopt different contours to comply with the local anatomy. For instance, as shown in FIG. 15A, the lower portion can define a compliant or flexible lip 47 projecting from one side of the lower rim 41a that can be used to navigate the retractor past a vessel or nerve.

Figure 16:
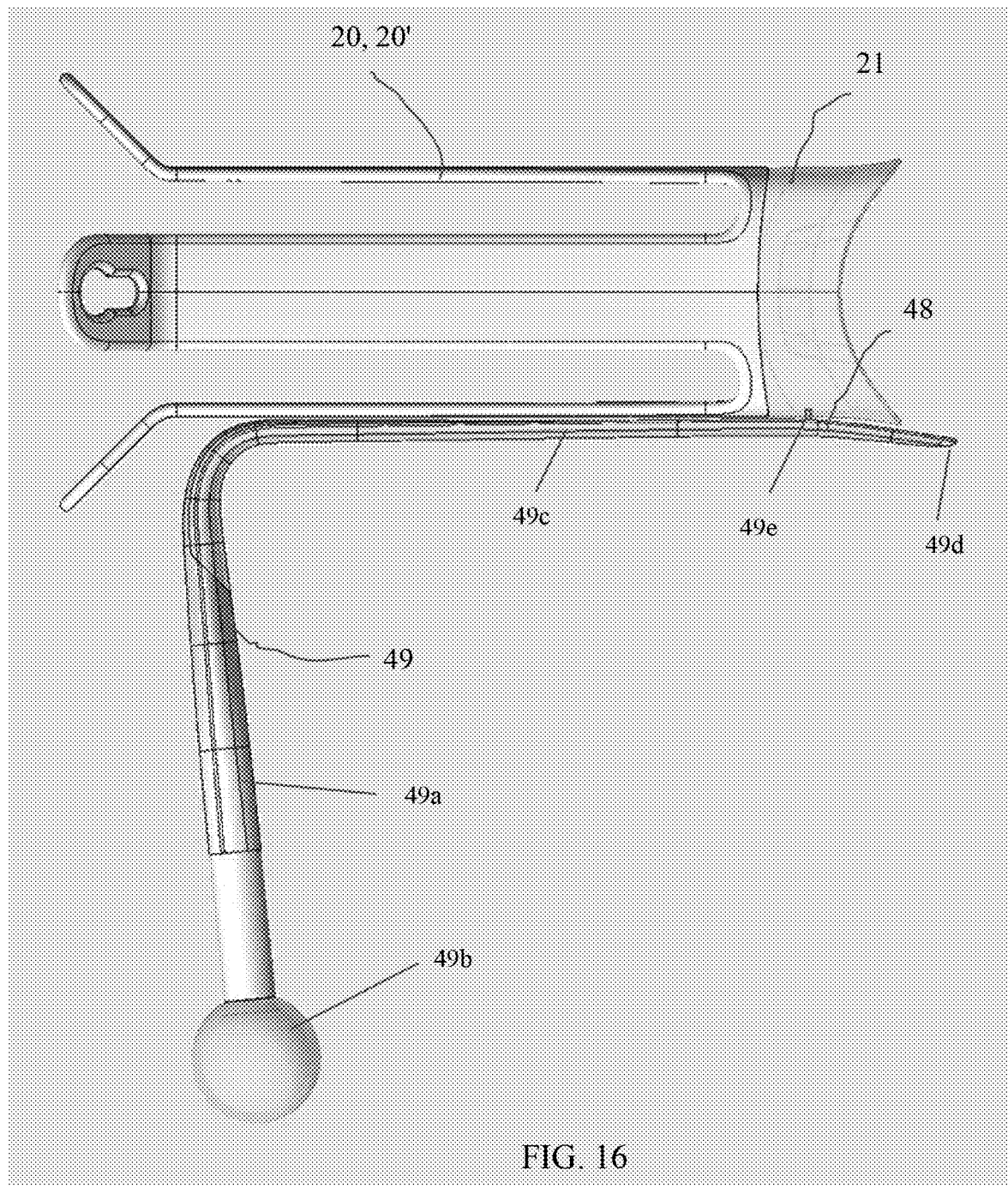
FIG. 16 is a side view of a retractor of the present disclosure engaged to a hand-held retractor.

The body 41 can define an attachment feature 48 for connecting to additional instruments or tool. Similar attachment features 48 can be provided on the outer surface of the body 21 of the retractor 20, 20', most particularly along the width of the retractor. The attachment points are configured to engage a hand-held retractor, such as the retractor 49 shown in FIG. 16. The attachment feature 48 can be configured as a key-slot, as shown in FIG. 15B, and the hand-held retractor 49 can incorporate a post 49e adapted to be received in the attachment point, similar to the post 14c (FIG. 14). The hand-held retractor includes a generally horizontal portion 49a that can be a rod terminating in a knob 49b configured for manual manipulation of the retractor from outside the patient's body. The horizontal portion 49a merges into a vertical portion 49c that can be a plate sized to extend along one of the legs of the retractor 20, 20'. The end portion 49d of the vertical portion 49c can be relatively more flexible than the remainder of the hand-held retractor 49 to reduce the risk of trauma to surrounding tissue when the retractor 49 is used to introduce a self-supporting retractor 20, 20'. The hand-held retractor can be used by the surgeon to navigate the retractor 20/20'/40 into position.

Figure 17:
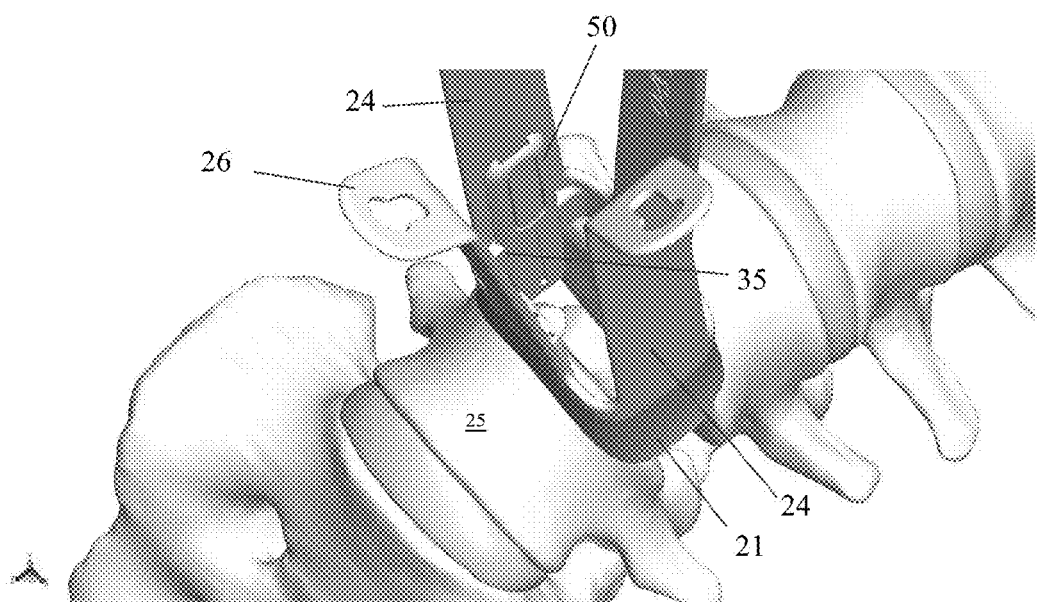
FIG. 17 is pictorial view of the retractor of FIGS. 13A-D in position during an anterior spinal surgery, and including a shim according to another feature of the present disclosure.

In a further feature of the retraction system disclosed herein, the retractor, particularly retractor 20', can be configured to engage and support shims. As described above, a shim can act as a distractor by contacting the endplates of the adjacent vertebral bodies and holding a disc space open. The shim can also help anchor the retractor in position as the adjacent vertebral bodies bear against the shim, holding it, and therefore the retractor attached to the shim, in place. In one embodiment, the end legs 24 of the retractor define an elongated recess 35 extending at least from the upper rim of the base 21 to the lower rim 22 and aligned with a corresponding leg (FIGS. 13B, 17). The recess 35 is thus in the form of a vertical channel that slidably receives a shim, such as the shim 50, shown in detail in FIGS. 18A-E. The shim 50 includes an elongated plate portion 52 that is sized to slide into the recess 35 on either leg 24, as shown in FIG. 17.

The lower portion 51 of the shim 50 is configured as a wedge or distractor. The shim is thus introduced into the retractor 20' when the rim 22 is seated on the adjacent vertebral bodies, with the lower portion 51 projecting below the rim 22, into the intervertebral space and in contact with the endplates of the adjacent vertebral bodies. The lower portion 51 not only anchors the retractor to the vertebral space but also helps distract and maintain the intervertebral space between the adjacent vertebral bodies. It is understood that the width of the lower portion 51 must be calibrated to the particular vertebral level and desired distance between the adjacent vertebral bodies. The recess 35 in the retractor 20' is thus wider than the maximum width distractor.

Figure 18A:
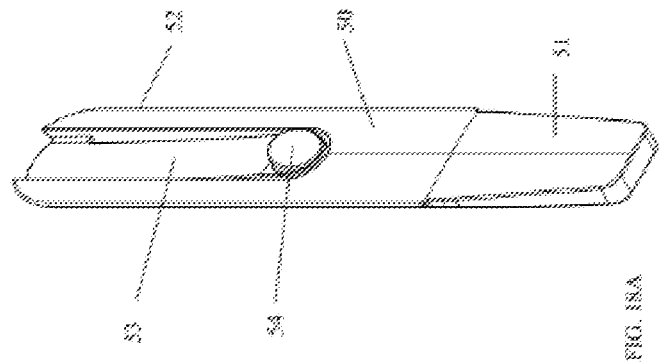
FIGS. 18A-E are perspective, side, edge and end views of the shim shown in FIG. 17.
Figure 18B:
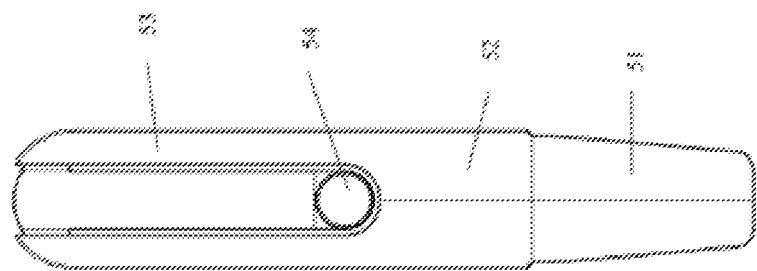
Figure 18C:
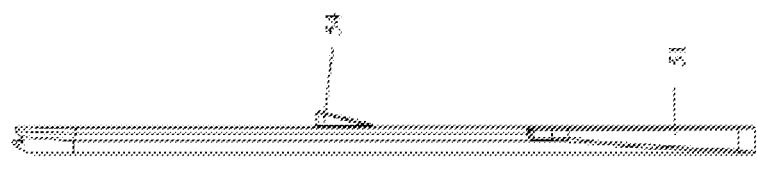
Figure 18E:
Figure 18D:
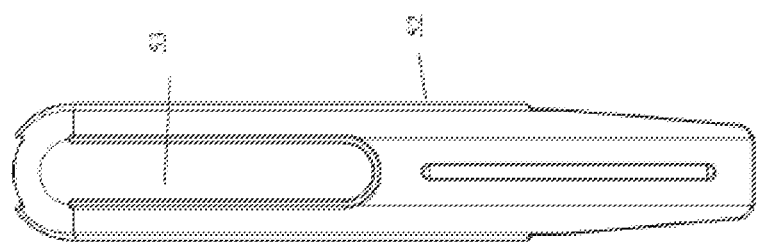

The distractor 50 is held in place by a resilient latch 53 and post 54 that can flex inward from the locking position shown in FIG. 18C. The latch flexes inward as the shim 50 is introduced into the recess 35 of the retractor 20' until the post 54 clicks into an indentation 55 (FIG. 13A) defined in the retractor. Other latching or locking mechanisms are contemplated to solidly attach a shim 50 to each leg 24.

Figure 19:
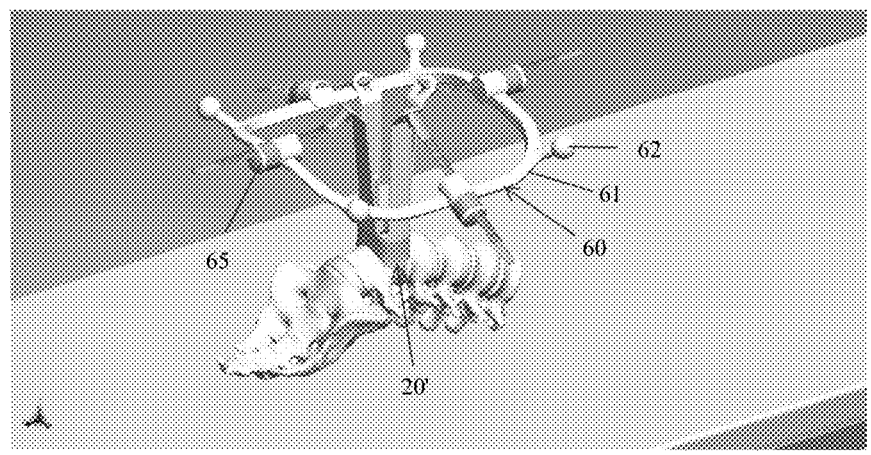
FIG. 19 is a pictorial representation of a self-supporting retractor system according to one embodiment of the present disclosure.

The present disclosure contemplates a self-supporting embodiment of the retractor 20', as shown in FIG. 19. In this embodiment, the retractor can be at least partially anchored to the vertebral bodies by pins or screws through bores 33, as described above, and then the legs 24, 26 can be maintained in a proper position by the frame assembly 60. The tension in the soft tissue surrounding the retractor can also help hold the retractor in position within the surgical site as the tissue bears against the legs 24/26 of the retractor. The frame assembly 60 includes a ring 61 that can be configured to encircle the surgical site, such as with a rectangular, trapezoidal, oval or circular shape. It is contemplated that the perimeter dimension of the ring 61 is calibrated to avoid impeding the surgeon's access to the working channel 23 within the retractor 20'. The frame is configured to engage an adjustable connector component 65, as described below. The frame can include projections 62 that are configured to be manually grasped to facilitate manipulation of the frame during installation of the self-supporting retractor. In addition, or alternatively, the projections 62 can serve as fiducials for imaging purposes and/or for use in connection with a surgical navigation system. In this instance, the projections 62 are at least coated with a material for imaging the projection, whether by an optical detector or by X-ray. It is further contemplated that similar fiducials may be incorporated into the retractor 20/20'/40 and/or shims 50 engaged to the retractor, provided that the fiducials are offset from the working space 23 at the surgical site. In one embodiment, a fiducial similar to the projection 62 can extend from the outer face of one or more of the legs 24/26, or a radio-opaque marker can be embedded within any part of the retractor or shims. The retractors disclosed herein are effectively anchored to the spine and remain anchored throughout the surgical procedure. Fiducials incorporated into the retractor and/or shims can be used to prevent errors in registration between the image used in the surgical navigation and/or to help register the images to the anatomy.

Figure 20:
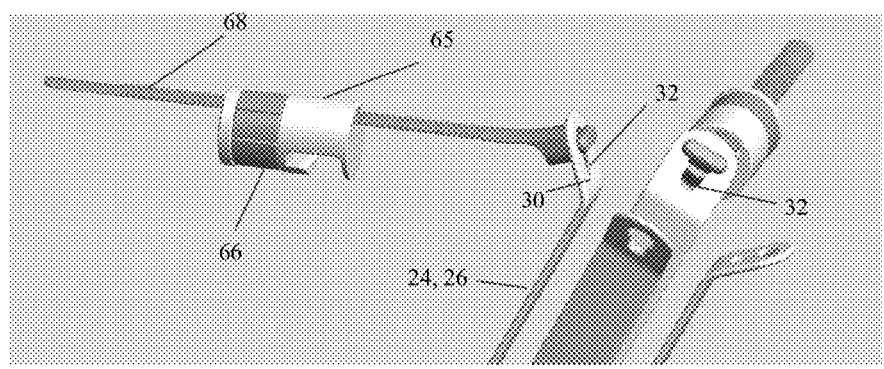
FIG. 20 is an enlarged view of components of the self-supporting retractor system shown in FIG. 19.

The adjustable connector component 65, shown in more detail in FIGS. 20-26, includes a barrel mechanism 66 that receives a flexible strap 68 therethrough, as shown particularly in FIGS. 20-21. The strap 68, shown in FIGS. 22A-22D, includes an elongated body 69 with a series of ridges 70 on one side of the body, similar to the well-known "zip tie". The strap terminates in an engagement portion 71 that includes a retainer bar 72 and an engagement groove 73. The retainer bar 72 is configured to be introduced in one orientation into the slot 32 (FIG. 12A) of the retractor legs 24, 26, and then rotated 90° to an orientation in which the retainer bar cannot pass through the slot. The tab 30 is engaged within the groove 73 to effectively clamp the engagement portion 71 onto the tab. In an alternative embodiment, the retainer bar 72 can be circular, in which case the slot 32 can have the configuration shown in FIG. 13A. In either configuration, the slot 32 and retainer bar 72 are configured to allow the retainer bar to enter the slot in one position and then latch onto the retractor leg in another position.

Figure 21C:
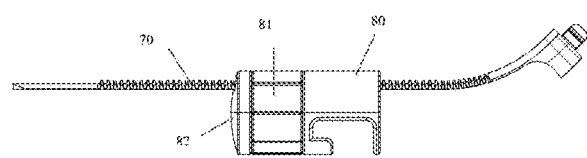
FIGS. 21A-D are perspective, bottom, side and end views of a barrel mechanism of the self-supporting retractor system shown in FIG. 19
Figure 21D:
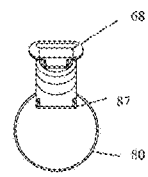
Figure 21B:
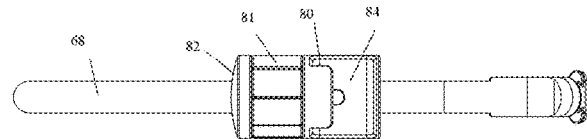
Figure 21A:
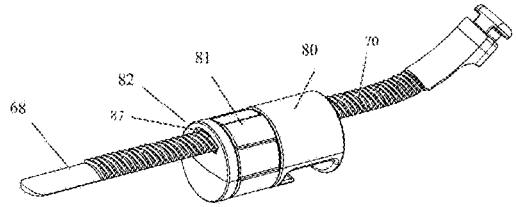
Figure 22D:
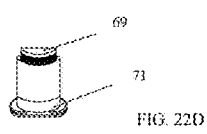
FIGS. 22A-D are perspective, bottom, side and end views of a strap of the self-supporting retractor system shown in FIG. 19.
Figure 22C:
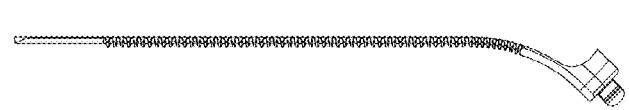
Figure 22B:
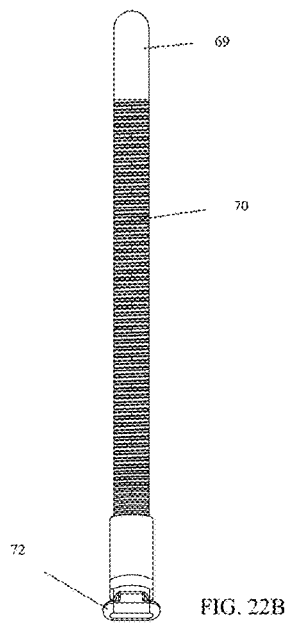
Figure 22A:
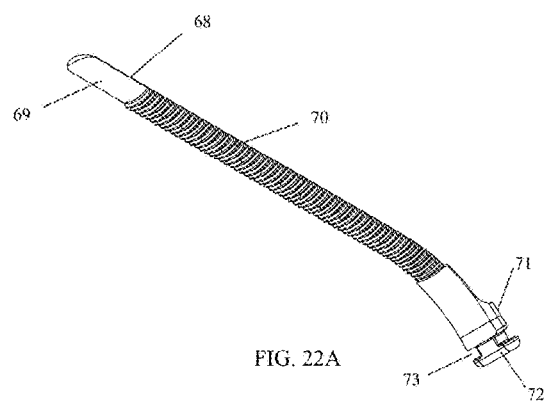

The barrel mechanism 66 includes a body 80, a barrel 81 and end cap 82, as depicted in FIG. 21A. As shown in the detail views of FIGS. 23A-D, the body 80 defines a slot 84 for receiving the ring 61, with a recess 86 formed inside the slot to retain the body on the ring when the components are tightened, as described herein. When the body 80 is mounted on the ring and the strap 68 is tightened, the ring is firmly seated in the recess 86 to hold the barrel mechanism in position. The body 80 further defines a channel 87 through which the strap is threaded, as depicted in FIG. 21A. A sliding surface 88 extends along the bottom of the channel 87 to provide support for the strap as it is engaged by the barrel 81. In one embodiment, the upper surface of the channel can be provided with features for engaging the ridges 70 of the strap 68 to control, but not prevent, longitudinal movement of the strap.

Figure 25C:
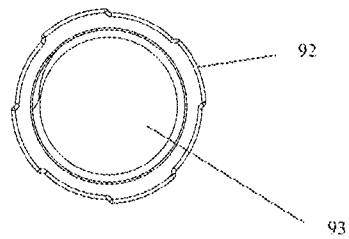
FIGS. 25A-D are perspective, bottom, side and end views of a barrel of the barrel mechanism shown in FIG. 21A-D.
Figure 25D:
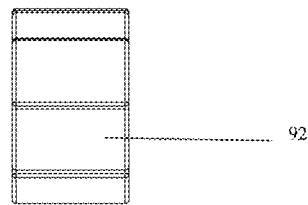
Figure 25B:
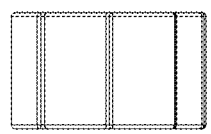
Figure 25A:
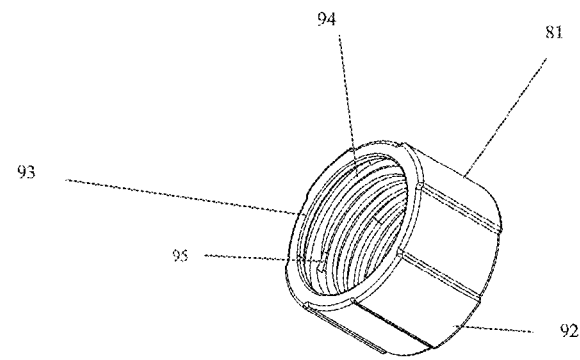

The body 80 also includes resilient mounting features 89 that are adapted to support the barrel 81 on the body. The barrel is provided with an external gripping feature 92 that allows the barrel to be manually gripped and rotated by the surgeon (FIGS. 25A, C). The inner circumferential surface 93 of the barrel includes surface features 94 defining a control portion configured to engage the ridges 70 of the strap to control longitudinal movement of the strap and with sufficient strength to maintain the strap in tension when the strap is tightened between the ring 61 and the retractor legs 24, 26. The control portion surface features 94 are essentially ratchets or ridges that engage the ridges 70 of the strap such that all longitudinal movement of the strap is prevented, thereby locking the connector component 65 to the ring 61. The resilient mounting features 89 are configured to allow the barrel 81 to be moved upward relative to the sliding surface 88 so that the ridges of the surface features 94 disengage from the ridges 70 of the strap 68. The mounting features 89 are thus configured as V-shaped legs projecting laterally outward from the body 80. The legs can be bent or deflected upward by moving the barrel 81 upward, but the legs still maintain pressure on the barrel from inside the barrel to hold the barrel in position on the body 81. The barrel can be moved upward until the inner circumferential surface 93 contacts the flanges 81a that are diametrically opposite the sliding surface 88 of the body. The resilience or "springiness" of the mounting features 89 push the barrel back into engagement with the strap 68 when manual pressure is released from the barrel.

In another embodiment, the barrel is supported by the mounting features 89 for rotation along the longitudinal axis of the barrel mechanism. In this embodiment, the barrel 81 is essentially a rotating nut that is mounted on the mounting features 89. In this embodiment, the interior of the barrel also includes a free portion 95 between the surface features 94 that does include the surface features and therefore does not engage the ridges of the strap so that the strap can move longitudinally freely through the channel 87. The barrel 81 can be rotated to a first position in which the free portion 95 is aligned with the ridges of the strap 68 so that the strap can be freely tightened. In this position, the surgeon can pull the elongated body 69 of the strap to place the strap in an initial tension. The surgeon can then rotate the barrel 80 until the control portion 84 is juxtaposed with the ridges 70 of the strap. The interface between the control portion 84 and the ridges 70 can be configured to pull the strap longitudinally with small rotations of the barrel 81 relative to the body 80, such as providing the control portions with a slight helical curvature, akin to internal threads. This configuration can allow fine tuning the tension of the assembled retractor system. In this embodiment, the barrel 81 can include external indicia to identify whether the barrel is in the first or second positions—i.e., whether the control portion 84 or the free portion 85 is aligned with the ridges 70 of the strap.

Figure 23C:
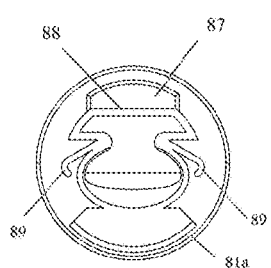
FIGS. 23A-D are perspective, bottom, side and end views of a body of the barrel mechanism shown in FIG. 19A-D.
Figure 23D:
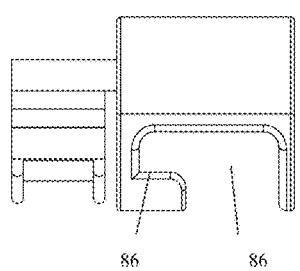
Figure 23B:
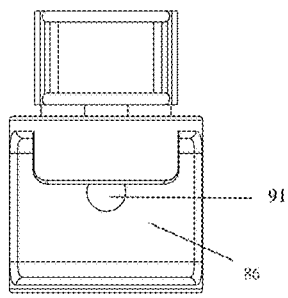
Figure 23A:
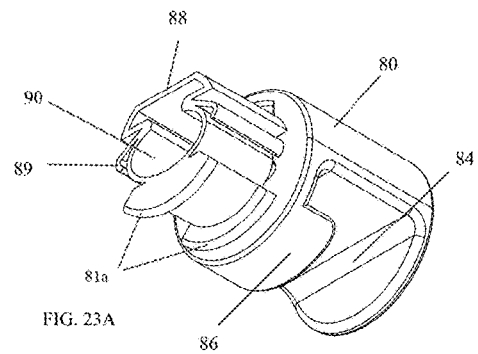
Figure 24:
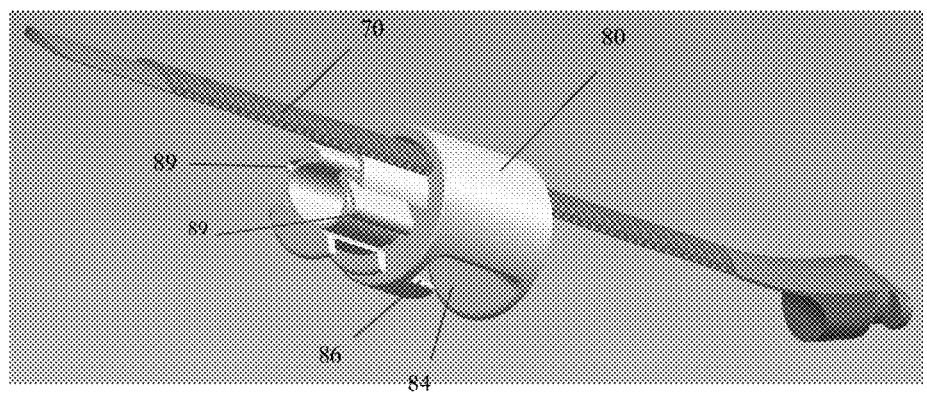
FIG. 24 is a perspective view of the body shown in FIGS. 23A-D with the strap of FIGS. 22A-D disposed therein.
Figure 26C:
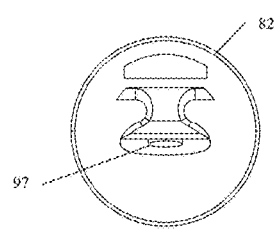
FIG. 26A-D are perspective, bottom, side and end views of an end cap of the barrel mechanism shown in FIG. 21A-D.
Figure 26D:
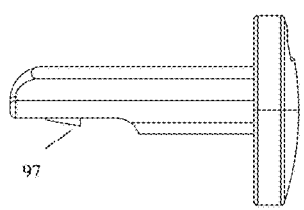
Figure 26B:
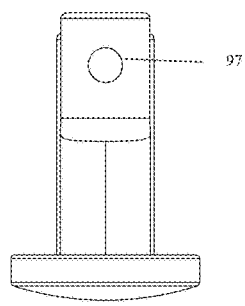
Figure 26A:
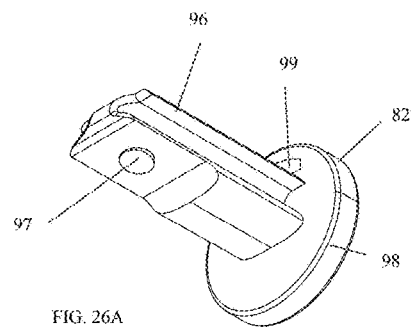

The assembly of the barrel mechanism 66 is completed by the end cap 82 shown in FIGS. 26A-26D. The end cap 82 includes an end plate 98 from which a mating body 96 projects, as shown in FIG. 26A. The mating body is configured to be received within a bore 90 defined in the body 80 of the barrel mechanism (FIG. 23A). A peg 97 engages an opening 91 (visible through the channel 86, as seen in FIG. 23B) in the body 80 to fix the end cap 82 to the body 80, with the barrel 81 sandwiched in between. The end plate defines a channel 99 that aligns with the channel 87 in the body 80 to receive the strap 68. It can be appreciated that the connector component 65 can be provided fully assembled to the surgeon, as depicted in FIG. 21A, with the barrel in the rotational position to hold the strap in place within the barrel mechanism.

As with the retractor, the entirety of the clamping component 65 is formed of a radio-transparent or radio-lucent material, such as plastic. The material for the ring 61 must be sufficiently rigid to provide the necessary support when the straps 68 are all placed in tension, but can still be formed of a translucent material.

In an alternative embodiment, a self-supporting system 60' is shown in FIG. 27 in which the ring 61' is directly mounted to a retractor, such as retractor 20'. In particular, the ring 61' is attached to the angled tab 30 at the end of each leg of the retractor 20'. The ring 61' can include downward posts (not shown) configured to engage the fixation features 32, which can be a key-slot configuration. In this embodiment, the legs 24, 26 of the retractor can be curved outwardly from the base of the retractor, as depicted in FIG. 27, so that the fixation features are aligned with the ring 61'. This feature allows the ring 61' to define essentially the same circumference as the ring 62 in FIG. 19. In this embodiment, the posts can have a circular head and the fixation features 32 can be configured as show in FIG. 13A to receive the circular head in the larger portion of the fixation feature.

Figure 28A:
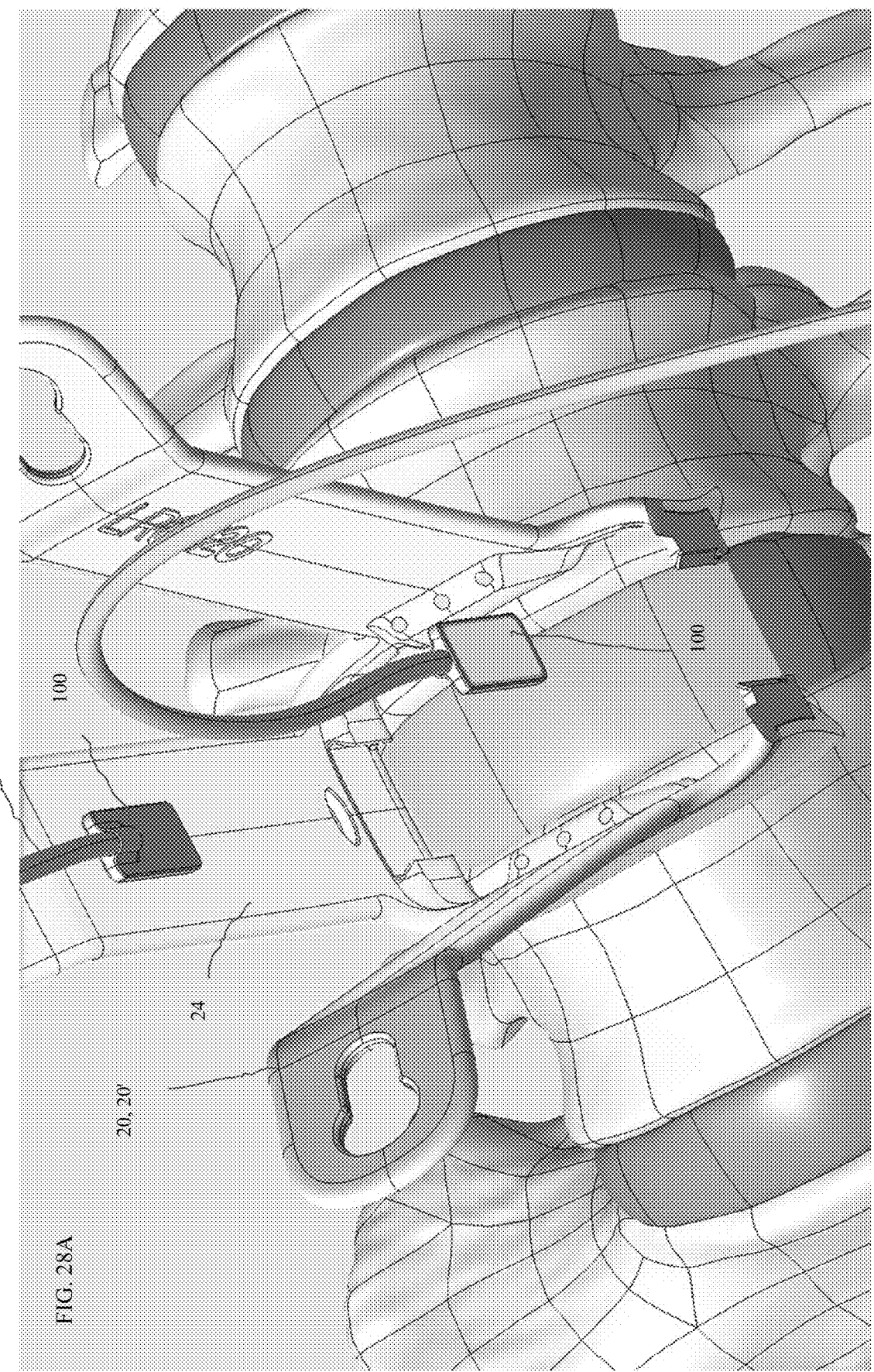
FIG. 28A, B is a perspective view of diffuse lighting systems used with the retractors disclosed herein.
Figure 28B:
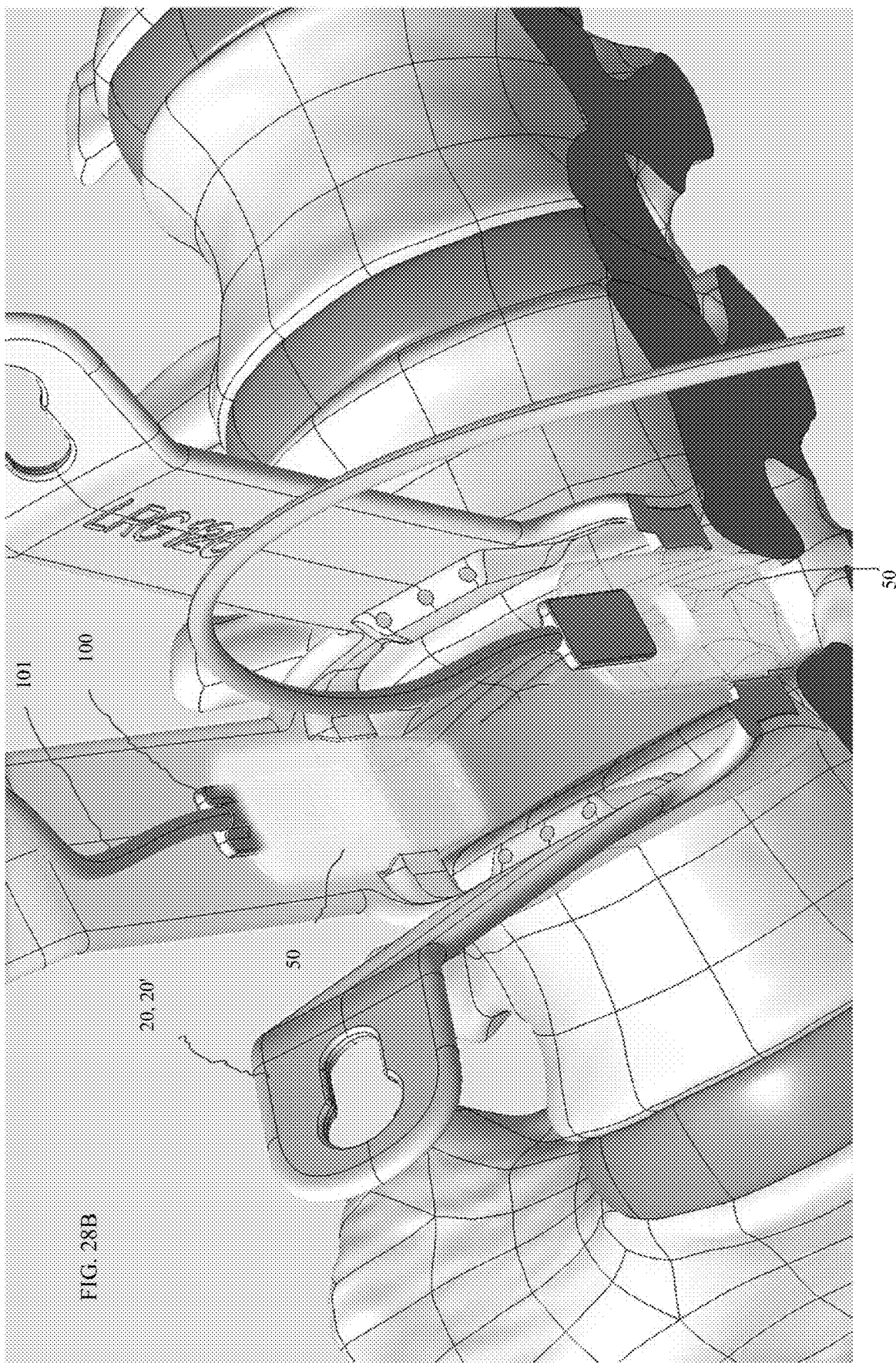

It is further contemplated that lighting elements are incorporated into the retraction system disclosed herein. The lighting elements can be mounted to the ring 11 of the fixed system or the ring 61 of the self-supporting system, or can be integrated into the legs 24, 26 of the retractor 20 or into the shims 50. Alternatively, or in addition to the ring-mounted lighting, lighting can be integrated into the retractor itself. In one embodiment, a light source 100 is integrated into the legs 24 of the retractor 20, 20' as shown in FIG. 28A, or into the shims 50, as shown in FIG. 28B. The portion of the legs or shim in which the light source is embedded can be formed of a translucent material, such as a plastic, that allows light to pass through the body and that diffuses the light to illuminate a surgical site. Light can be conveyed to the light source 100 by a light transmission component 101, which can be a light pipe or fiber optic cable as is known in the art. This approach does not increase the overall bulk or envelop of the retractor and provides significant lighting for the surgeon.

Figure 29:
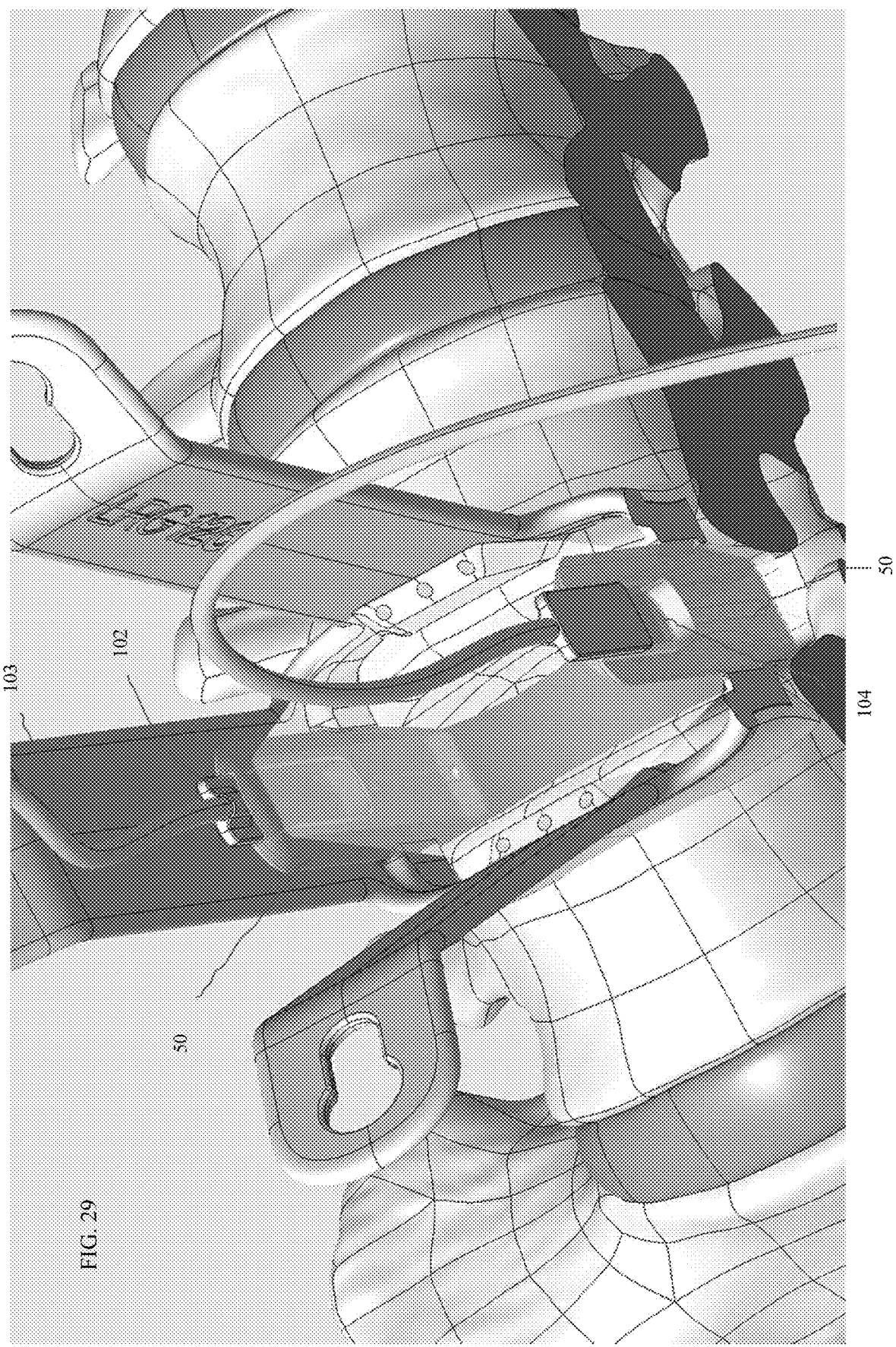
FIG. 29 is a perspective view of a direct lighting system used with the retractors disclosed herein.

Alternatively, or in addition, a directional light 102 can be incorporated into a shim 50, as shown in FIG. 29. The light 102 can be mounted within a recess 104 in the shim and connected to light pipe or fiber optic cable 103 in a conventional manner. In this embodiment, the light 102 shines directly onto the surgical site, rather than being diffused as in the prior embodiments.

It is contemplated that rather than constitute a light source, the components 100 or 102 can be a visualization device, such as a camera or optical detector, that permits visualization of the surgical site within the retractor. Thus, in one embodiment, two such components 100/102 are provided, with one component constituting a light source and the other component constituting a visualization device. The image detected by the visualization device can be transmitted along the transmission component 101 to a receiver (not shown) that can be used to display the image for the surgeon's benefit during the procedure.

An alternative retractor 110, shown in FIGS. 30A-B, is similar to the retractors 20, 20', but modified to permit adjustment of two legs of the retractor. The retractor 110 includes a base 111 with legs 112 extending from the sides of the retractor, similar to the legs 26 of the retractor 20' (FIG. 13D). However, rather than the fixed legs 24, the legs 115 are pivotable within a channel 117 defined in the base 111 of the retractor. The interface between the pivot end 116 of the leg 115 and the channel 117 allows the leg to be moved from one side of the retractor (FIG. 38A) to the other (FIG. 38B). This feature allows the surgeon to tailor the location of the legs 115 based on the anatomy being retracted and/or on the angle of approach that the surgeon is taking to access the spine. It is contemplated that the pivot interface between end 116 and channel 117 can allow the leg 115 to be pivoted at any time during the surgery and as needed by the surgeon to access the site. The interface between the pivot end 116 and the channel 117 can be a close running fit or a friction fit that permits limited movement of the leg 115 but provides a sufficient frictional engagement between the components to hold the position of the leg once adjusted by the surgeon. Alternatively, a separate fixation mechanism can be incorporated into the pivot interface to lock the leg 115 into a particular orientation.

The present disclosure should be considered as illustrative and not restrictive in character. It is understood that only certain embodiments have been presented and that all changes, modifications and further applications that come within the spirit of the disclosure are desired to be protected.

What is claimed is:

1. A surgical retractor for retracting soft tissue and anatomy at a spinal surgical site, comprising:
   a rectangular tubular base defining a long axis, an upper rim, a lower rim and a working channel between the upper and lower rims, the base and lower rim sized and configured to be seated along the long axis on adjacent vertebral bodies spanning an intervertebral space; and
   at least two elongated legs, each of said two elongated legs integrally formed with said base and each of said two elongated legs projecting from said upper rim in a direction perpendicular to said long axis and each including a fixation feature at a free end thereof, each of said at least two legs having a length sufficient for the fixation feature to be outside the body of a patient when the lower rim is seated on adjacent vertebral bodies of the patient,
   wherein said base and said at least two legs are formed of a radio-transparent or radio-lucent material.

2. The surgical retractor of claim 1, wherein said tubular base includes:
   an upper portion defining said upper rim; and
   a lower portion defining said lower rim and connected to said upper portion,
   wherein said lower portion is relatively more flexible than said upper portion.

3. The surgical retractor of claim 2, wherein said upper portion and said lower portion are integrally formed.

4. The surgical retractor of claim 1, wherein said tubular base includes two or more portions having different flexibilities relative to each other.

5. The surgical retractor of claim 1, wherein said lower rim has a length and a width, and defines a concave curvature along said length sized to correspond to the curvature of a vertebral body.

6. The surgical retractor of claim 5, wherein said base defines at least one bore extending from said upper rim to said concave curvature of said lower rim, said at least one bore sized to receive an anchoring pin for anchoring the retractor to a vertebral body.

7. The surgical retractor of claim 1, wherein said base defines at least one bore extending from said upper rim to said lower rim, said at least one bore sized to receive an anchoring pin for anchoring the retractor to a vertebral body.

8. The surgical retractor of claim 1, wherein each of said two legs includes an end defining said fixation feature, said end angled outward relative to said base.

9. The surgical retractor of claim 1, further comprising a light source mounted to at least one of said at least two legs, said light source arranged to direct light into said working channel.

10. The surgical retractor of claim 9, wherein said light source is embedded within said at least one of said at least two legs, and said at least one of said at least two legs is at least partially formed of an optically translucent material.

11. The surgical retractor of claim 9, further comprising a visualization component mounted to at least one of said at least two legs, said visualization component configured to visualize the surgical site through the working channel.

12. The surgical retractor of claim 1, further comprising:
   said tubular base defining at least one elongated recess extending from said upper rim to said lower rim and aligned with a corresponding leg of said retractor; and
   an elongated shim having an elongated plate portion slidably received within said at least one elongated recess and an integral lower portion extending below said lower rim when said elongated plate portion is seated within said at least one recess, said lower portion having a width sized to contact the endplates of the adjacent vertebral bodies when the surgical retractor is seated on the vertebral bodies.

13. The surgical retractor of claim 12, further comprising a resilient latch for removable engagement between said tubular base and said elongated plate portion of said shim.

14. The surgical retractor of claim 12, further comprising a light source mounted to one or more of said elongated shim and at least one of said at least two legs, said light source arranged to direct light into said working channel.

15. The surgical retractor of claim 14, further comprising a visualization component mounted to at least one or more of said elongated shim and at least one of said at least two legs, said visualization component configured to visualize the surgical site through the working channel.

16. The surgical retractor of claim 1, wherein:
   said tubular base defines at least one channel extending from said upper rim; and at least one of said at least two legs includes a pivot end opposite said free end, said pivot end pivotably received in said at least one channel of said tubular base.

17. A surgical retractor system comprising:
a surgical retractor according to claim 1;
a frame; and
at least two brackets, each mountable between said frame and said fixation feature of a corresponding one of said at least two legs.

18. The surgical retractor system of claim 17, further comprising a connector component for engaging each of said at least two brackets to said frame.

19. The surgical retractor system of claim 18, wherein:
each of said at least two brackets is an elongated strap having;
an engagement portion at one end configured to engage said fixation feature of said corresponding one of said at least two legs; and
a series of ridges at an opposite end thereof; and
said connector component is configured to selectively engage said series of ridges to fix said elongated strap relative to said connector component and to selectively disengage said series of ridges to permit movement of said elongated strap relative to said connector component.

20. The surgical retractor system of claim 19, wherein said connector component includes:
a body defining a channel through which said elongated strap extends; and
a barrel rotatably mounted to said body in alignment with said series of ridges of said elongated strap, said barrel defining internal surface features configured to engage said series of ridges when said barrel is in a first position and an internal free portion that does not engage said series of ridges when said barrel is in a second position.

21. The surgical retractor system of claim 17, wherein said frame is a rigid ring.

22. The surgical retractor system of claim 21, wherein said frame includes a projection extending from said rigid ring, said projection configured to be manually grasped to manipulate said rigid ring.

23. The surgical retractor system of claim 22, wherein said projection is at least coated with a material detectable by an optical sensor or by X-ray.

24. The surgical retractor of claim 1, wherein each of said two elongated legs is integrally formed with said upper rim.

25. The surgical retractor of claim 1, wherein:
said tubular base has a height from said lower rim to said upper rim; and
each of said at least two elongated legs has a length from said upper rim to said fixation feature that is greater than said height.

26. The surgical retractor of claim 25, wherein:
said height is between 4 and 6 cm; and
said length is between 15 and 20 cm.

* * * * *